United States Patent [19]

Dexter et al.

[11] 4,116,930

[45] Sep. 26, 1978

[54] PYROMELLITIC DIMIIDES OF 3,5-DIALKYL-4-HYDROXYPHENYLSUB-STITUTED AMINES

[75] Inventors: Martin Dexter, Briarcliff Manor; Martin Knell, Ossining; Peter Klemchuk, Yorktown Heights; John F. Stephen, New City, all of N.Y.

[73] Assignee: Ciba-Geigy Corporation, Ardsley, N.Y.

[21] Appl. No.: 723,128

[22] Filed: Sep. 14, 1976

Related U.S. Application Data

[63] Continuation of Ser. No. 628,259, Nov. 3, 1975, abandoned, which is a continuation-in-part of Ser. No. 450,540, Mar. 12, 1974, abandoned, which is a continuation of Ser. No. 186,499, Oct. 4, 1971, abandoned.

[51] Int. Cl.² ............................................. C08K 5/34
[52] U.S. Cl. ........................ 260/45.8 N; 260/45.85 S; 260/326 C
[58] Field of Search ................... 260/326 C, 45.85 N, 260/45.8 N

[56] References Cited

U.S. PATENT DOCUMENTS 3,536,670   10/1970   Aelony et al. ............... 260/326 C X

OTHER PUBLICATIONS

Chem. Abstracts, 67:116726d.

Primary Examiner—Ethel G. Love
Attorney, Agent, or Firm—Vincent J. Cavalieri

[57] ABSTRACT

Pyromellitic diimides of 3,5-dialkyl-4-hydroxyphenyl-substituted amines of this invention effectively stabilize organic materials against the effects of heat and oxygen. The diimides of this invention are prepared by reacting the appropriate 3,5-dialkyl-4-hydroxyphenylsubstituted amine with pyromellitic anhydride or pyromelletic diimide. An example of this class of stabilizer is N,N'-bis(3,5-di-t-butyl-4-hydroxyphenyl)pyromellitic diimide.

9 Claims, No Drawings

PYROMELLITIC DIIMIIDES OF 3,5-DIALKYL-4-HYDROXYPHENYLSUBSTITUTED AMINES

This is a continuation application of Ser. No. 628,259 filed on Nov. 8. 1975, which in turn is a continuation-in-part of Ser. No. 450,540, filed Mar. 12, 1974, which in turn is a continuation of Ser. No. 186,499, filed Oct. 4, 1971 all now abandoned.

DETAILED DESCRIPTION

This invention relates to novel pyromellitic diimide derivaties of 3,5-dialkyl-4-hydroxyphenylsubstituted amines which are useful as stabilizers for organic polymeric materials which are subject to thermal and oxidative deterioration. The compounds of this invention are represented by the formula:

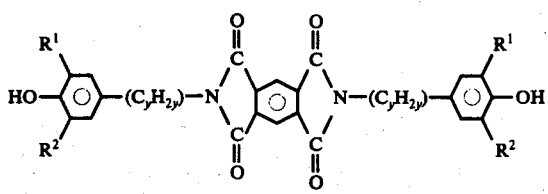

wherein each of $R^1$ and $R^2$ is the same or different (lower) alkyl group of from 1 to 4 carbon atoms; and $y$ has a value of from 0 to 3.

Illustrative examples of (lower) alkyl groups of from 1 to 4 carbon atoms which are represented by $R^1$ and $R^2$ are methyl, ethyl, propyl, isopropyl, butyl and t-butyl. The preferred groups are methyl, isopropyl and t-butyl. Especially preferred t-butyl groups.

The compounds of formula 1 wherein $y$ is 0, 2 and 3 can be prepared by reacting a 3,5-dialkyl-4-hydroxyphenylsubstituted amine of the formula

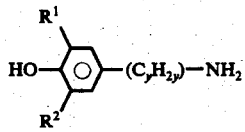

wherein $R^1$ and $R^2$ is as defined previously, with pyromellitic dianhydride in an inert solvent such as dichlorobenzene at reflux temperatures.

The compounds of formula 1 wherein $y$ is 1 can be prepared by reacting 3,5-dialkyl-4-hydroxybenzyl dialkyl amine of the formula

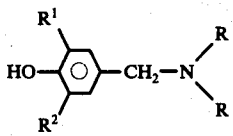

wherein $R^1$ and $R^2$ are as defined previously and R is an alkyl group as methyl or ethyl, with pyromellitic diimide in an inert solvent such as dimethyl formamide at approximately 120° C.

The 3,5-dialkyl-4-hydroxyphenylsubstituted amines wherein $y$ is 0 can be prepared as described in U.S. Pat. No. 3,198,797.

The amine, when $y$ is 2 can be prepared for example through chloromethylation of a dialkyl phenol as described in U.S. Pat. No. 2,838,571, followed by treatment with sodium or potassium cyanide and reduction of the resultant dialkylhydroxyphenyl acetonitrile to the amine. The amine wherein $y$ is 3 can be prepared by reducing 3(3,5-dialkyl-4-hydroxyphenyl)propionitrile with lithium aluminum hydride to yield the corresponding amine. The nitrile can be prepared according to the method described in U.S. Pat. No. 3,121,732 wherein the appropriate dialkylphenol is reacted with acrylonitrile. The 3,5-dialkyl-4-hydroxybenzyldialkylamine of formula III can be prepared as described by E.P. Previc et al, Industrial and Engineering Chemistry, Vol. 53, No. 6, Page 469, June 1961.

The compounds of this invention are stabilizers of organic material normally subject to thermal and oxidative deterioration. weight which are thus stabilized include synthetic organic polymeric substances such as vinyl resins formed from the polymerization of vinyl halides or from the copolymerization of vinly halides with unsaturated polymerizable compounds, e.g., vinylesters, α,β-unsaturated ketones, α,β-unsaturated aldehydes, and unsaturated hydrocarbons such as butadienes and styrene; poly-α-olefins such as polyethylene, polypropylene, polybutylene, and the like, including copolymers of poly-α-olefins; polyurethanes and polyamides such as polyhexamethylene adipamide and polycaprolactam; polyesters such as polyethylene terephthalates; polycarbonates; polyacetals; polystyrene; polyethyleneoxide; polyisoprene; polybutadiene and copolymers such as those of high impact polystyrene containing copolymers of butadiene and styrene and those formed by the copolymerization of acrylonitrile, butadiene and/or styrene.

In general, one or more of the stabilizers of the present invention are employed in amounts, in toto, of from about 0.005 to about 5% by weight of the composition to be stabilized. A particularly advantageous range of the present stabilizers is from about 0.05% to about 2%. The preferred range is particularly effective in polyolefins such as polypropylene.

These compounds may be incorporated in the polymer substance during the usual processing operations, for example, by milling, or extrusion. The stabilized polymer can be fabricated into films, fibers, filaments, hollow-spheres and the like. The heat stabilizing properties of these compounds advantageously stabilize the polymer against degradation during such processing at the high temperatures generally encountered.

The stabilizers employed in this invention can also be used in combination with other stabilizers or additives. Especially useful co-stabilizers are dilauryl-β-thiodipropionate and distearyl-β-thiodipropionate.

The following formula represents co-stabilizers which are in certain instances very useful in combination with the stabilizers of this invention:

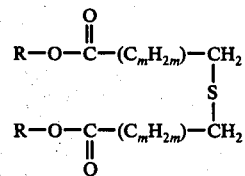

wherein R is a alkyl group having from 6 to 24 carbon atoms; and $m$ is an integer from 1 to 6. The above co-stabilizers are used in the amount of from 0.01 to 2% by weight of the organic material, and preferably from 0.1 to 1%.

Other antioxidants, antiozonants, thermal stabilizers, ultraviolet light absorbers, coloring materials, dyes, pigments, metal chelating agents, etc., may also be used in the compostions in combination with the stabilizers of the invention.

The following are presented to further illustrate the present invention without introducing any limitation thereto.

EXAMPLE 1

N,N'-bis(3,5-di-t-butyl-4-hydroxyphenyl)pyromellitic diimide

The reaction flask was charged with 11.05 grams of 4-amino-2,6-d-t-butylphenol, 5.45 grams of pyromellitic dianhydride and 100 ml. of o-dichlorobenzene. The reaction mixture was heated to reflux for approximately 2 hours using a Dean Stark trap to remove the water formed. After cooling, the mixture was filtered and washed with petroleum ether. The filter cake was dried and dissolved in 200 ml. of boiling glacial acetic acid and filtered. The product which crystallized on cooling, was filtered, washed with acetic acid, and dried in vacuum over phosphorous pentoxide and potassium hydroxide. The product had a melting point of 304°–306° C.

Analysis for $C_{38}H_{44}N_2O_6$: % Calculated: C, 73.05; H, 7.10. % Found: C, 73.37; H, 7.41.

EXAMPLE 2

N,N,-bis[2-(3,5-di-t-butyl-4-hydroxyphenyl)ethyl]pyromellitic diimide

By substituting an equivalent amount of 3,5-di-t-butyl-4-hydroxyphenylethylamine for 4-amino-2,6-di-t-butylphenol in the procedure of Example 1, the corresponding N,N'-bis(3,5-di-t-butyl-4-hydroxyphenylethyl)pyromellitic diimide is obtained which has a melting point of 231°–233° C.

Analysis for $C_{42}H_{52}N_2O_6$: % Calculated: C, 74.09; H, 7.70; N, 4.11; O, 14.10. % Found: C, 73.55; H, 7.40; N, 4.12.

In a similar manner, by subtituting an equivalent amount of 3-(3,5-di-t-butyl-4-hydroxyphenyl)propylamine for 4-amino-2,6-di-t-butylphenol in the above procedure the corresponding N,N'-bis[3-(3,5-di-t-butyl-4-hydroxyphenyl)propyl] pyromellitic diimide is obtained.

EXAMPLE 3

N,N'-bis(3,5-di-t-butyl-4-hydroxybenzyl) pyromellitc diimide

To 100 ml. of dimethylformamide were added 10.8 grams of pyromellitic diimide and 27.6 grams of 3,5-di-t-butyl-4-hydroxybenzyldimethylamine. The reaction mixture was heated under a nitrogen atmosphere at 120° to 125° C for 21 hours. After cooling, the reaction mixture was poured into water. The material obtained was extracted with ether and the crystalline product which remained was recrystallized from ethyl cellosolve and then from benzene-heptane (1:1). The product obtained had a melting point of 274°–276° C.

Analysis for $C_{40}H_{48}N_2O_6$: % Calculated: C, 73.59; H, 7.41; N, 4.29; O, 14.71. % Found: C, 73.50; H, 7.38; N, 4.28.

In a similar manner, by substituting 3-methyl-5-t-butyl-4-hydroxybenzyldimethylamine for 3,5di-t-butyl-4-hydroxybenzyldimethylamine there is obtained N,N'-bis(3-methyl-5-t-butyl-4-hydroxybenzyl)pyromellitic diimide with a melting point of 267°–269° C.

EXAMPLE 4

Unstabilized polypropylene powder (Hercules Profax 6501) was thoroughly blended with 0.20 percent by weifht of various compounds of this invention. Also prepared were samples of polypropylene containing 0.1 percent by weight of the stabilizers and 0.3 percent by weight of distearylthiodipropionate (DSTDP). The blended materials were then milled on a two-roll mill at 182° C for 10 minutes.

The milled polyproylene sheets were then cut into pieces and pressed for 7 minutes at 218° C, on a hydraulic press at 500 psi and then transferred to a cold press at 500 psi. Samples of the resulting 25 mil sheet were tested for resistance to accelerated aging in a forced draft oven at 150° C. The results are set out in Table I below:

TABLE I

| Additive(s) | Oven Aging at 150° Hours to Failure |
|---|---|
| 0.2% of N,N'-bis(3,5-di-t-butyl-4-hydroxybenzyl)pyromellitic diimide | 50 |
| 0.1% of N,N'-bis(3,5-di-t-butyl-4-hydroxybenzyl)pyromellitic diimide + 0.3% DSTDP | 1335 |
| 0.1% of N,N'-bis(3-methyl-5-t-butyl-4-hydroxybenzyl)pyromellitic diimide + 0.3% 0f DSTDP | 1715 |
| 0.1% of N,N'-bis[2-(3,5-di-butyl-4-hydroxyphenyl)ethyl]pyromellitic diimide + 0.3% DSTDP | 1790 |
| Unstabilized Polypropylene | 3 |
| 0.3% DSTDP* alone | <20 |

*distearylthiodipropionate (a synergist for phenolicantioxidants)

The above data clearly indicates the significant increase in the stabilization of polypropylene upon addition of the anitioxidants of the present invention.

Stabilized polypropylene compositions are also obtained when 0.5% of N,N'-bis[3-(3,5-di-t-butyl-4-hydroxyphenyl)propyl]pyromellitic diimide and N,N'-bis(3,5-di-t-butyl-4-hydroxyphenyl)pyromellitic diimide respectively are employed alone or in combination with DSTDP.

EXAMPLE 5

To 39.3 g (0.15 moles) of hexamethylenediammonium adipate were added 0.177 g (7.5 × 10⁻⁴ mole; 0.5 mole percent) of hexamethylenediammonium diacetate as molecular weight control agent and 0.183 g (0.5% of theoretical nylon yield) of various compounds of this invention. The mixtures were mixed thoroughly and added to Pyrex polymer tubes.

The polymer tubes were evacuated three times and filled with high purity nitrogen each time. The polymer tubes with a continuously maintained, slightly positive nitrogen pressure were placed in a methyl salicylate vapor bath at 222° C. The nylon-6,6 salt melted with bubbling due to the liberation of water. After bubbling ceased, a clear melt was obtained which solidified afer 5–8 minutes. After 1 hour at 222° C the polymer tubes were transferred to an o-phenylphenol bath at 285° C for 1 hour where the solid gradually remelted. The polymer tubes were kept in the 285° C vapor bath for an additional + hour while they were maintained under oil pump vacuum (<1 mm). High Purity nitrogen was then readmitted and the polymer tubes were allowed to cool.

The stabilized nylon-6,6 obtained was ground in a Wiley mill at ambient temperature. About 2 g were heated in a small glass Petri dish in a circulating air, rotary oven at 140° C for 65 hours. The viscosities of 1% sulfuric acid solutions of aged and unaged polymer samples were determined at 25° C. Stabilizer effectiveness was judged by the percent retention of specific viscosity and by color formation after oven aging. A polyamide containing no stabilizers was prepared and tested in a similar manner and their results with respect to the percent retention of specific viscosity is compared in the following Table II. The stabilized polyamides had better percent retention of specific viscosity and color retention than the unstabilized polyamide after oven aging.

Table II

| Polyamide | Specific Viscosity Percent Retention |
|---|---|
| Unstabilized | 65±5 |
| N,N'-bis(3,5-di-t-butyl-4-hydroxyphenyl)pyromellitic diimide | 84 |
| N,N'-bis[2-(3,5-di-t-butyl-4-hydroxyphenyl)ethyl]pyromellitic diimide | 83 |

Stabilized polyamide compositions are prepared in a similar manner as above with the following stabilizers:
(a) 0.5% of N,N'-bis(3,5-di-t-butyl-4-hydroxybenzyl)pyromellitic diimide
(b) 0.5% of N,N'-bis(3-methyl-5-t-butyl-4-hydroxybenzyl)pyromellitic diimide
(c) 0.5% of N,N'-bis(3,5-di-t-butyl-4-hydroxyphenylpropyl)pyromellitic diimide Stabilized compositions are also obtained when 0.5% of the aforementioned stabilizers are incorporated into nyon-6,6 flakes before extrusion.

EXAMPLE 6

A quantity of SBR emulsion containing 100 g of rubber (500 ml of cold SBR type 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 5% NaCl solution which has been acidified with HCl to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ¼ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm.) at 40°-45° C).

The dried rubber (25 g) is heated under nitrogen at 125° in a Brabender mixer and to this is added with mixing 0.125 g (0.5%) of N,N'-bis[2-(3,5-di-t-butyl-4-hydroxyphenylethyl]pyromellitic diimide. The composition is mixed for 5 minutes after which it is cooled and compression molded at 125° C into 5 inches × 5 inches × 0.25 inch plagues.

The plaques are placed on aluminum sheets and heated in a circulating air oven at 100° C for up to 96 hours. The viscosity of a 0.5% toluene solution of aged and unaged rubber samples are determined at 25° C. Stabilizer effectiveness is judged by the percent retention of specific viscosity, color formation and gel content after oven aging. The stabilized rubber has better viscosity, color retention and less gel content then the rubber which is unstabilized after oven aging.

Similar results are obtained when N,N'-bis(3, 5-di-t-butyl-4-hydroxybenzyl)pyromellitic diimide is used in place of the above mentioned stabilizer in the rubber composition.

EXAMPLE 7

A composition comprising linear polyethylene and 0.10% by weight of N,N'-bis(3,5-d-t-butyl-4-hydroxyphenyl) pyromellitic diimide retains its physical properties at 120° C longer than one which does not contain the stabilizer.

1. A compound of the formula

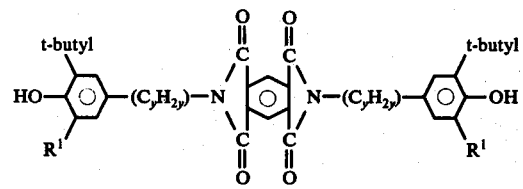

wherein $R^1$ is tert-butyl group, and $y$ has a value from 0 to 3.

2. A compound of the formula

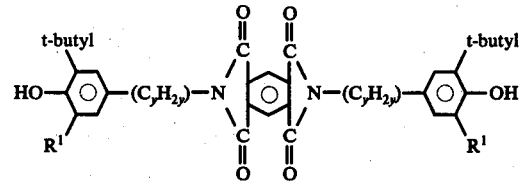

wherein $R^1$ is selected from methyl, isopropyl and tert-butyl groups, and $y$ has a value from 1 or 2.

3. The compound according to claim 1 which is N,N'-bis(3,5-di-t-butyl-4-hydroxyphenyl)pyromellitic diimide.

4. The compound according to claim 1 which is N,N'-bis[2-(3,5-di-t-butyl-4-hydroxyphenyl)ethyl]pyromellitic diimide.

5. The compound according to claim 1 which is N,N'-bis(3,5-di-t-butyl-4-hydroxybenzyl)pyromellitic diimide.

6. The compound according to claim 1 which is N,N'-bis(3-methyl-5-t-butyl-4-hydroxybenzyl)pyromellitic diimide.

7. A composition of matter stabilized against oxidative deterioration which comprises a synethetic organic polymeric material normally subject to oxidative deterioration containing from 0.005 to 5% by weight of a stabilizing compound according to claim 1.

8. A composition of claim 7 wherein the organic polymeric material is a polyolefin.

9. A composition of claim 8 wherein the polyolefin is polypropylene.

* * * * *